United States Patent [19]
Ino et al.

[11] Patent Number: 5,969,262
[45] Date of Patent: *Oct. 19, 1999

[54] METHOD AND APPARATUS FOR TESTING JUNCTION STRENGTH OF ELECTRODE

[75] Inventors: Koji Ino, Kariya; Yusuke Watanabe, Obu, both of Japan

[73] Assignee: Denso Corporation, Kariya, Japan

[ * ] Notice: This patent is subject to a terminal disclaimer.

[21] Appl. No.: 08/972,685

[22] Filed: Nov. 18, 1997

[30] Foreign Application Priority Data

Nov. 19, 1996 [JP] Japan .................................. 8-308495

[51] Int. Cl.⁶ ..................................................... G01N 3/08
[52] U.S. Cl. ................................................. 73/827; 73/831
[58] Field of Search .............................. 73/827, 831, 826, 73/830, 834, 845, 850, 851

[56] References Cited

U.S. PATENT DOCUMENTS

| | | |
|---|---|---|
| 3,213,667 | 10/1965 | Gettys . |
| 3,724,265 | 4/1973 | LaValle ..................... 73/827 |
| 3,945,248 | 3/1976 | West . |
| 4,213,556 | 7/1980 | Persson et al. . |
| 4,282,758 | 8/1981 | Wootten et al. . |
| 4,453,414 | 6/1984 | Ronemus et al. . |
| 4,745,684 | 5/1988 | Brown et al. . |
| 5,214,963 | 6/1993 | Widder . |
| 5,374,808 | 12/1994 | Coultrip et al. . |
| 5,641,913 | 6/1997 | Watanabe . |

FOREIGN PATENT DOCUMENTS 2 194 844  3/1988  United Kingdom .

*Primary Examiner*—Max Noori
*Attorney, Agent, or Firm*—Pillsbury Madison & Sutro LLP

[57] ABSTRACT

A probe made of copper and supported by a movable arm via a load cell and a jig has a joining surface having good wettability with solder at the tip end thereof and has a covering portion having poor wettability with the solder around the circumferential periphery. The solder and flux are stuck to the joining surface and the solder is put into contact with a bump electrode to be tested on a substrate in this state. Then, the solder is melted by an induction heating coil and then cooled down and solidified to join the bump electrode to be tested to the probe. The bump electrode is broken by pulling up the probe in this state at a constant speed and at the same time the pulling force exerted on the probe is measured by the load cell.

15 Claims, 3 Drawing Sheets

METHOD AND APPARATUS FOR TESTING JUNCTION STRENGTH OF ELECTRODE

BACKGROUND OF THE INVENTION

1. Field of the Invention

The present invention relates to a method and an apparatus for testing the junction strength of an electrode formed on the surface of a substrate, for example, a bump electrode formed on a flip chip IC, to evaluate the junction strength of the same.

2. Description of Related Art

For example, U.S. Pat. No. proposes directly testing the junction strength of soldered bump electrodes by directly pulling the soldered bump electrodes on a flip chip IC with a pointed probe one by one. To be more specific, the above-described U.S. patent discloses a process comprising providing that a probe made of material having good wettability with solder, such as copper, striking the tip end of the probe in or pressing the end of the probe on the soldered bump electrode, heating the probe to melt the bump electrode, and cooling and solidifying to join the probe to the soldered bump electrode, and exerting a pulling force on the probe when the probe is pulled in a junction state. The pulling force is measured by a load cell.

However, in cases in which the above-described apparatus is actually used, it often has large variations in the measurement results and, hence, generally reduces reliability. Through experimental tests and analyses, it was found that those variations are caused by the amount of solder between the probe and the soldered bump electrode.

That is, since in this apparatus the junction between the probe and the bump electrode is made only at the soldered portion for composing the electrode, the amount of solder for joining the probe and bump electrode is relatively reduced. In the state in which the amount of solder for joining the probe to the electrode is small, the junction strength between them is apt to be insufficient and, hence, there may be many cases in which the junction strength between the probe and the bump electrode is smaller than that of the bump electrode to an IC substrate.

Moreover, it was found also that, even if sufficient junction strength between the probe and the bump electrode is provided, when the probe is pulled in the state where the amount of solder for joining the probe to the bump electrode is small, stress concentration is produced at the portion the cross sectional area of which is reduced by the deformation caused by the pulling and the above-described solder is broken before the bump electrode is separated from the substrate. That is, in the state where the small amount of solder is small, as described above, there may be cases where the pulling strength of the soldered portion is smaller than the junction strength of the bump electrode to the IC substrate. In such cases, it is also difficult to accurately measure the junction strength of the soldered bump electrode.

Furthermore, the above apparatus has the drawbacks that an object to be tested is limited to a soldered bump electrode having solder on the surface layer thereof and, hence, it is difficult to evaluate the junction strength of a gold-made bump electrode or a copper-made electrode, which results in the lessened range of applications.

SUMMARY OF THE INVENTION

The present invention has been achieved in consideration of the above-described drawbacks and has an object to provide a method and an apparatus for testing the junction strength of an electrode by accurately measuring the junction strength of the electrode formed on the surface of a substrate to thereby improve the reliability of test results and extend the range of applications.

To accomplish the above-described object, according to the testing method and apparatus of the present invention, when the junction strength of an electrode formed on the surface of a substrate is tested, in the state in which the predetermined amount of solder is previously stuck to a joining surface which is formed on the probe and has good wettability with the solder, the solder is melted by a heater and then is cooled down and solidified to join the electrode to be tested to the probe with the solder. The pulling force exerted on the probe when the probe is moved in the direction that separates the probe from the electrode to be tested in such a junction state is measured.

In this case, the sufficient amount of solder to tightly join the electrode to be tested to the probe can be stuck to the joining surface and, hence, there is less likelihood that the junction strength between the electrode to be tested and the probe is insufficient or that the pulling strength of the soldered portion is insufficient. Therefore, when the probe is moved in the direction that separates the probe from the electrode to be tested, the possibility the junction state between the electrode to be tested and the probe being carelessly released or the soldered portion being carelessly broken is avoided and, hence, the junction strength of the electrode to be tested is accurately measured, which improves the reliability for the test.

Moreover, even if the solder is not on the electrode to be tested, the electrode to be tested is tightly joined to the probe with the solder previously stuck to the joining surface and, hence, the limitations to the kinds of electrode to be tested are eliminated, which expands the range of applications. Furthermore, since the solder is previously stuck to the joining surface, the deterioration of wettability with the solder caused by the oxidization of the joining surface can be prevented beforehand and, hence, the junction created by the solder between the electrode to be tested and the probe can always be kept in an acceptable state, which improves the reliability for the test in this aspect.

Preferably, the area of the joining surface is set larger than the area of the surface opposite to the joining surface of the electrode to be tested. In this case, when the solder previously stuck to the joining surface is melted, the solder is apt to flow around the periphery of the electrodes to be tested and, hence, the junction strength between the electrode to be tested and the probe can be made still higher, which can further improve the reliability for the test.

More preferably, a covering portion comprising material having poor wettability with the solder is formed around the joining surface of the probe. In this case, there is no fear that the useless solder is stuck to the periphery of the joining surface of the probe and, hence, the amount of solder required to test the strength of the electrode can be reduced to the minimum value.

Still more preferably, the covering portion is made of chromium or titanium. In this case, it can be reliably prevented that the solder is uselessly stuck to the probe.

BRIEF DESCRIPTION OF THE DRAWINGS

Additional objects, features and advantages of the present invention will become more apparent from the following detailed description when read with reference to the accompanying drawings, in which.

DESCRIPTION OF THE PREFERRED EMBODIMENTS

An embodiment of a testing method and apparatus according to the present invention will be described hereinafter with reference to the accompanying drawings.

Figure 1:
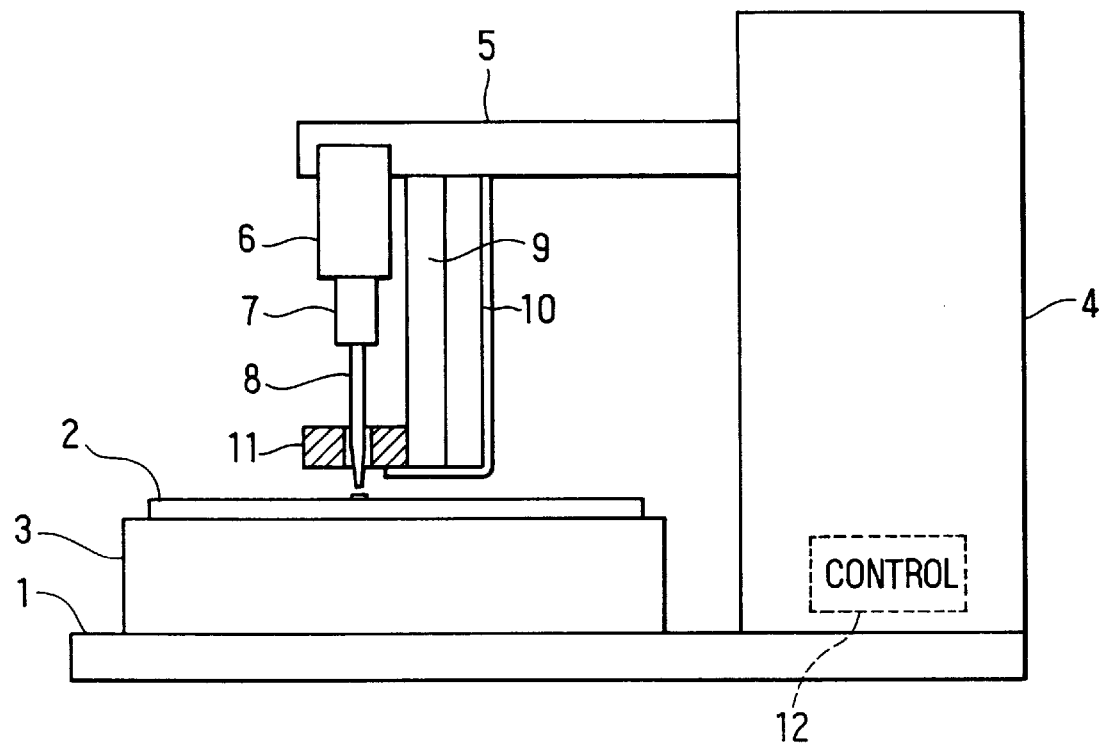
FIG. 1 is a side view showing a testing apparatus of an embodiment according to the present invention.

In FIG. 1, the testing apparatus has a mounting table 3 for mounting a substrate 2 which is to be tested (for example, a semiconductor wafer or a semiconductor chip) and a main body unit 4 on a base 1. A movable arm 5 is supported in a state in which it projects in parallel with the mounting table 3 from the side of the main body unit 4 and is driven by a driving mechanism (not shown) installed in the main body unit 4 and can be moved up and down and in a horizontal direction (in three dimensional directions of X, Y, Z axes).

The movable arm 5 has a load cell 6 on the tip end thereof. A probe 8 is connected to the load cell 6 via a jig 7 so that the pulling force exerted on the probe 8 can be measured by the load cell 6.

Moreover, a supporting arm 9 is vertically fixed to the lower side of the movable arm 5 and the supporting arm 9 has on the tip end thereof a cooling nozzle 10 for blowing nitrogen gas from a cooling device (not shown) and an induction heating coil 11 for melting solder stuck on a joining surface 8a (FIG. 2) formed on the tip end of the probe 8. Further, although not shown specifically, a position adjusting mechanism for adjusting the relative position of the probe 8 to the induction heating coil 11 is mounted and, when a current is passed through the induction heating coil 11, the tip end of the probe 8 is positioned in the induction heating coil 11 by the position adjusting mechanism.

A control device 12 is installed in the main body unit 4 and the control device 12 executes the moving control of the movable arm 5 by the above-described driving mechanism (not shown), electric power on/off control to the induction heating coil 11 and a nitrogen gas blowing control (cooling control) by the cooling device (not shown), based on a predetermined computer program. Moreover, the control device 12 is programmed to calculate the pulling force exerted on the probe 8 based on the output of the load cell 6 and display the calculated results on a display (not shown).

Figure 2:
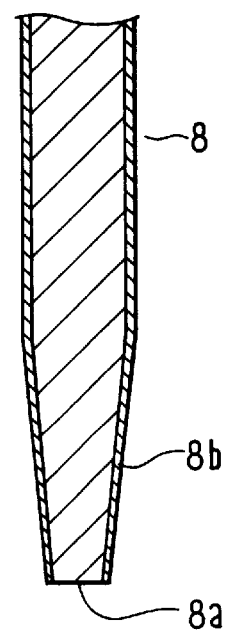
FIG. 2 is a longitudinal sectional view showing a portion of a probe used in the embodiment shown in FIG. 1.

As shown in FIG. 2, the probe 8 is made of copper and is shaped like a needle of circular cross section and has the joining surface 8a having good wettability with solder on the tip end thereof. The joining surface 8a is formed in a flat surface shape at a right angle to the axial direction and its diameter is 50 to 300 μm larger than the diameter of a generally circular bump electrode, for example, an electrode to be tested and designated by numeral 2a in FIGS. 3C and 3D, that is, the area of the joining surface 8a is larger than the area of the surface opposite to the joining surface 8a of the bump electrode 2a.

Moreover, it is preferable that a solder film is previously stuck to the joining surface 8a to prevent the joining surface 8a from being oxidized. The material of the probe is not limited to copper and a metal having good wettability with the solder and good heat conductivity, such as copper, copper alloy, gold, silver, 42-alloy (42% Ni—Fe) or the like, may be used.

The periphery of the joining surface 8a of the probe 8, that is, the circumferential periphery of the probe 8 is covered with a covering portion 8b made of the material having poor wettability with the solder, such as chromium, titanium, nickel-chromium alloy, or the like. In this embodiment, the covering portion 8b is formed by coating the circumferential periphery of the probe 8 with chromium or titanium by using a plating method or a vacuum disposition method.

The present embodiment having the above-described construction will operate as follows with the control by the control device 12.

Figure 3A:
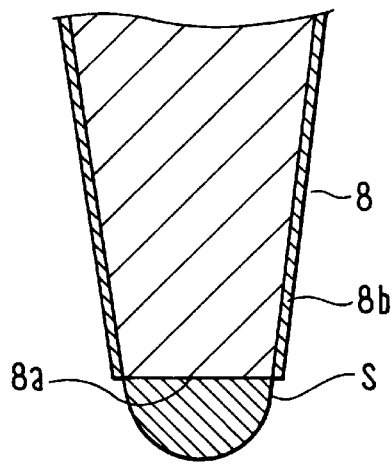
FIGS. 3A through 3D are longitudinal sectional views showing operational steps for the embodiment shown in FIG. 1.

That is, when the control device 12 tests the junction strength of the bump electrode 2a on the substrate 2, the control device 12 moves the probe 8 over a melted solder tank (not shown) and dips the tip end of the probe 8 in the melted solder and picks the melted solder up, whereby the solder S is stuck to the joining surface 8a in a semispherical shape, as shown in FIG. 3A. In this case, since the covering portion 8b having poor wettability with the solder is formed on the periphery of the joining surface 8a, the solder is not stuck to the covering portion 8b.

Figure 3B:
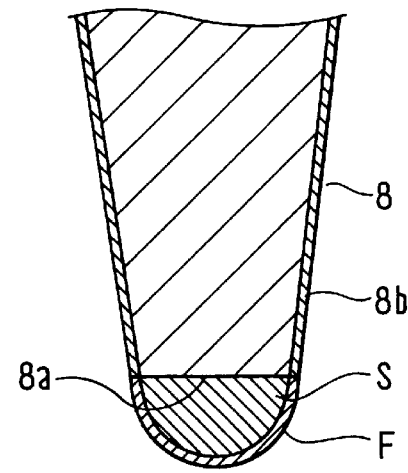

Next, the control device 12 blows nitrogen gas from the cooling nozzle 10 on the tip end part of the probe 8 to solidify the solder S stuck on the joining surface 8a and then, as shown in FIG. 3B, sticks flux F to cover the outer surface of the solder S on the joining surface 8a.

Figure 3C:
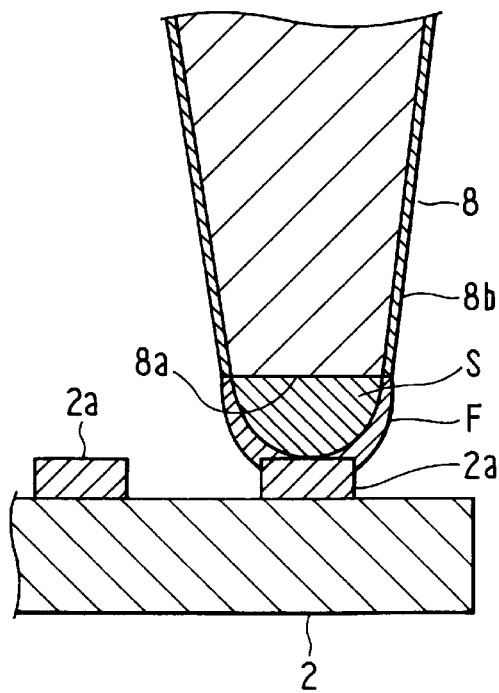

Thereafter the control device 12 moves the probe 8 over the bump electrode 2a to be tested on the substrate 2. The control device 12 controls the probe 8 such that the central axis of the probe 8 and the central axis of the bump electrode 2a are on the same axis and then lowers the probe 8 to put the solder S stuck to the joining surface 8a into contact with the bump electrode 2a to be tested, as shown in FIG. 3C.

Figure 3D:
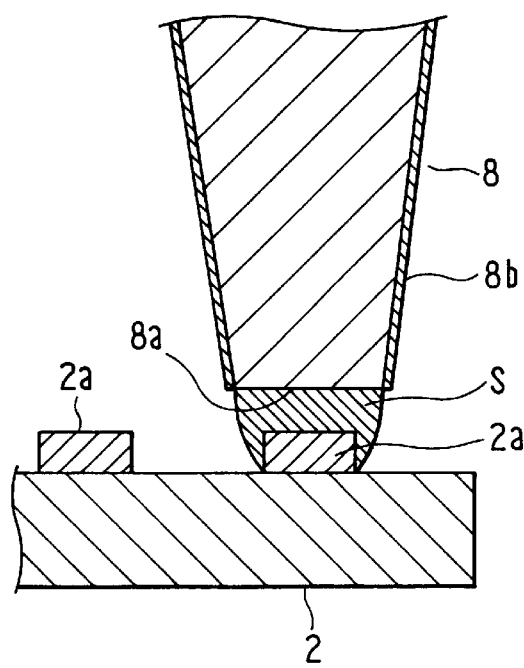

In this contact state, the control device 12 passes a current through the induction heating coil 11 to melt the solder S and blows the nitrogen gas from the cooling nozzle 10 on the tip end part of the probe 8 to cool the stuck solder S to the ordinary temperature, whereby the solder is solidified, which results in a state in which the bump electrode 2a is joined to the probe 8 with the solder S, as shown in FIG. 3D.

The control device 12 moves the probe 8 upward in the direction which separates from the bump electrode 2a by moving up the probe 8 at a constant speed to break the bump electrode 2a to be tested and calculates the pulling force exerted on the probe 8 based on the measuring output of the load cell 6 and displays the calculated results on the display (not shown). Accordingly, the junction strength of the bump electrode 2a to the substrate 2 can be evaluated based on the displayed value of the display.

In this embodiment, since a sufficient amount of solder for tightly joining the bump electrode 2a to the probe 8 can be stuck to the joining surface 8a of the tip end of the probe 8, there is less likelihood that the junction strength between the bump electrode 2a and the probe 8 might be insufficient. Moreover, there is less likelihood that the pulling strength of the solder S might be insufficient.

Therefore, when the probe 8 is moved in the direction which separates from the bump electrode 2a, the accidental releasing of the junction between the bump electrode 2a and the probe 8 can be prevented assuredly and the accidental breaking of the solder S can be prevented also. As a result, the measurement of the junction strength of the bump electrode 2a can be conducted accurately, which improves reliability for the test.

In this connection, as described above, to accurately measure the junction strength of the bump electrode, it is predicated that, letting P be the strength of the junction between the joining surface 8a and the solder S and T be the tensile strength of the solder S and B be the junction strength of the bump electrode 2a, these P, T, and B satisfy two relations B<T and B<P. According to the construction of the present embodiment, the above two equations can be easily satisfied by predetermining the amount of solder S to be stuck to the joining surface 8a.

Figure 4:
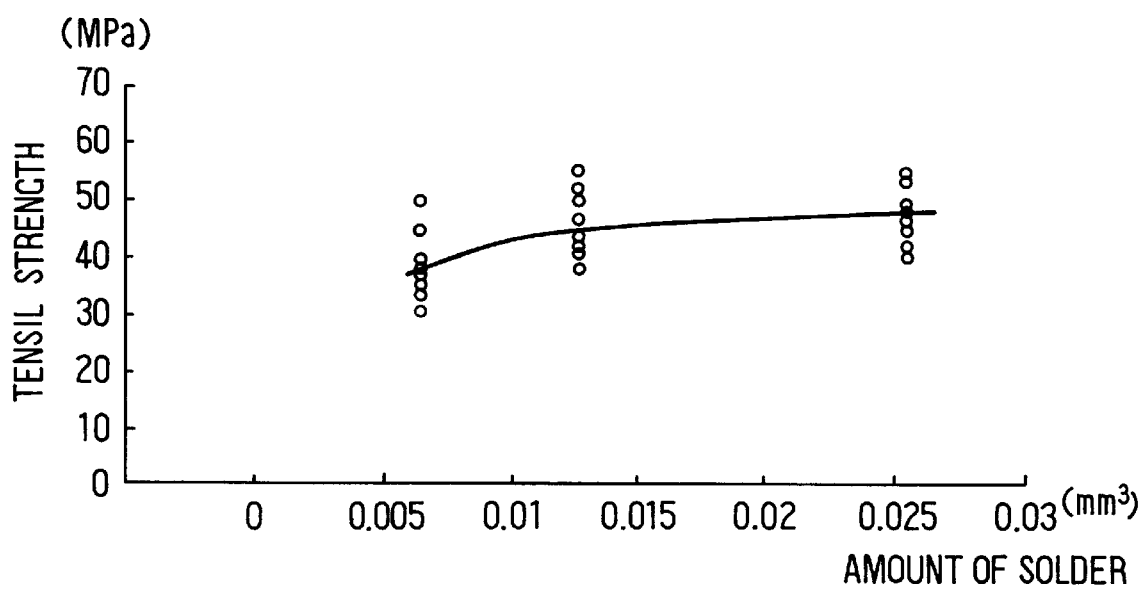
FIG. 4 is a graph showing test results of the embodiment.

As a result of experimental testing conducted on the above-described embodiment, the following measurement result was produced as shown in FIG. 4. The test result shows the measured junction strength (tensile strength) of an electrode for a plurality of test pieces having a bump electrode made of copper formed in a circular shape while the amount of solder S used for joining the joining surface 8a to the bump electrode is being changed. This testing was carried out on test pieces having a bump electrode of 220 μm in diameter and a joining surface 8a of 350 μm in diameter by using the solder of 40Sn/60Pb.

As is evident from FIG. 4, if the amount of the solder S used for joining the joining surface 8a to the bump electrode is not less than 0.015 mm³, the change in the tensile strength becomes saturated. Therefore, when the bump electrode 2a to be tested is a bump electrode made of copper, if the amount of the solder S previously stuck to the joining surface 8a is at least about 0.015 mm³, the variations in the test results of the tensile strength are reduced to thereby improve reliability for the tests. Moreover, if the bump electrode 2a to be tested is a soldered bump electrode, it is preferred that the total amount of the solder on the soldered bump electrode side and the solder S be not less than about 0.015 mm³.

Moreover, according to the construction of the present embodiment, even if the solder is not on the bump electrode 2a to be tested, the bump electrode 2a can be tightly joined to the probe 8 with the solder S previously stuck to the joining surface 8a to thereby remove restrictions on the kinds of electrode to be tested, which extends the range of applications. Further, since the solder is previously stuck to the joining surface 8a, the wettability with the solder is prevented from being deteriorated by the oxidization of the joining surface 8a made of copper and, hence, the junction state by the solder between the bump electrode 2a and the probe 8 can be kept in good state, which further improves the reliability for the test.

Further, since the area of the joining surface 8a is set larger than the area of the surface opposite to the joining surface 8a of the bump electrode 2a to be tested, when the solder S previously stuck to the joining surface 8a is melted, the solder S easily flows around the bump electrode 2a to be tested, as shown in FIG. 3D and, hence, the junction strength between the bump electrode and the probe 8 is further increased, which still further improves the reliability for the test.

Since the covering portion 8b comprising chromium or titanium having extremely bad wettability with the solder is formed around the joining surface 8a of the probe 8 (around the probe 8), the covering portion 8b can prevent the solder from uselessly sticking to the periphery of the joining surface 8a of the probe 8, which can reduce the amount of solder required to test the strength of the electrode to the minimum value. In this case, since the covering portion 8b is formed by coating the periphery of the probe 8 with chromium or titanium by using a plating method or a vacuum deposition method, the covering portion 8b can be easily formed.

Furthermore, since the solder S stuck to the joining surface 8a is melted by the induction heating coil 11, the heat for fusing the solder S is hard to transfer to the load cell 6 side through the probe 8, which, as a result, advantageously eliminates the possibility of the elevated temperature of the load cell 6 adversely affects on the measured output of the load cell 6.

The solder in the present embodiment may include not only Pb—Sn alloy but all other kinds of brazing metals. In the present embodiment, the solder S stuck to the joining surface 8a is forcibly cooled down by nitrogen gas, but the solder S may be naturally cooled down.

In the embodiment, the solder S stuck to the joining surface 8a is melted while contacting the bump electrode 2a to be tested and then is cooled down and solidified to join the bump electrode 2a to the probe 8. However solder S previously stuck to the joining surface 8a may be melted and then put into contact with the bump electrode to be tested and be cooled down to join them.

The solder S is stuck to the joining surface 8a by dipping the tip end of the probe 8 in the melted solder tank, but a flux containing solder paste may be stuck to the joining surface 8a in advance. The induction heating coil is used as a heater, but a heater for directly heating the probe 8 may be used. The material which has good wettability with the solder and is hard to oxidize like gold may be plated on the joining surface 8a. It is not necessarily required that the diameter of the joining surface 8a be larger than the diameter of the bump electrode 2a but it may be nearly equal to the diameter of the bump electrode 2a. Even if the movable arm 5 can be moved only up and down, the junction strength of the electrode can be measured.

An example of the bump electrode on a semiconductor wafer (or a semiconductor chip) has been described as an electrode to be tested, but the junction strength of other electrodes can also be tested. That is, this embodiment may be applied further to the test of the junction strength of an electrode which is formed on a ceramic substrate or a resin substrate and made of metal having good wettability with the solder (for example, land independently formed on the substrate) or a bump electrode mounted on a chip part such as a chip condenser, a chip resistance or the like.

Still further, the present invention is not limited to the embodiment having been described hereinabove but may be modified or expanded in other ways without departing from the spirit of the invention.

We claim:

1. A method for testing a junction strength of an electrode formed on a surface of a substrate, said method comprising the steps of:

providing a probe formed with a joining surface having good wettability with solder;

sticking a predetermined amount of solder to the joining surface of said probe;

heating to melt said solder while maintaining said solder in contact with said electrode to be tested;

joining said electrode to be tested to said probe by cooling down and solidifying said solder stuck to said joining surface after melting the solder;

moving said probe in a direction to separate said probe from said electrode to be tested; and measuring a pulling force exerted on said probe during said moving of said probe.

2. A method for testing a junction strength of an electrode as claimed in claim 1, wherein said joining surface has an area larger than that of a surface opposite to said joining surface of said electrode to be tested.

3. A method for testing a junction strength of an electrode as claimed in claim 1, wherein said probe has a covering portion formed from material having poor wettability with said solder and formed around a circumferential periphery of said joining surface.

4. A method for testing a junction strength of an electrode as claimed in claim 3, wherein said material forming said covering portion is chromium or titanium.

5. A method for testing a junction strength of an electrode as claimed in claim 1, wherein said predetermined amount of said solder is at least 0.015 mm$^3$.

6. A method for testing a junction strength of an electrode formed on a surface of a substrate, said method comprising the steps of:

provided a probe formed with a joining surface having good wettability with solder;

sticking a predetermined amount of solder to the joining surface of said probe;

contacting said solder with said electrode to be tested while maintaining said solder in melted condition by heating;

joining said electrode to be tested to said probe by cooling down and solidifying said solder stuck to said joining surface after melting the solder;

moving said probe in a direction to separate said probe from said electrode to be tested; and measuring a pulling force exerted on said probe during said moving of said probe.

7. A method for testing a junction strength of an electrode as claimed in claim 6, wherein said joining surface has an area larger than that of a surface opposite to said joining surface of said electrode to be tested.

8. A method for testing a junction strength of an electrode as claimed in claim 6, wherein said probe has a covering portion formed from material having poor wettability with said solder and formed around a circumferential periphery of said joining surface.

9. A method for testing a junction strength of an electrode as claimed in claim 8, wherein said material forming said covering portion is chromium or titanium.

10. A method for testing a junction strength of an electrode as claimed in claim 6, wherein said predetermined amount of said solder is at least 0.015 mm$^3$.

11. An apparatus for testing a junction strength of an electrode formed on the surface of a substrate, said apparatus comprising:

a probe formed with a joining surface having good wettability with solder;

heating means for heating and melting solder stuck to the joining surface of said probe;

moving means for moving said probe;

controlling means for joining said electrode to be tested to said probe with said solder stuck to said joining surface and for moving said probe in a direction to separate said probe from said electrode to be tested; and measuring means for measuring pulling force exerted on said probe when said probe is moved in the direction to separate from said electrode to be tested.

12. An apparatus for testing a junction strength of an electrode as claimed in claim 11, wherein said joining surface has an area larger than that of a surface opposite to said joining surface of said electrode to be tested.

13. An apparatus for testing a junction strength of an electrode as claimed in claim 11, wherein said probe has a covering portion formed from material having poor wettability with said solder and formed around a circumferential periphery of said joining surface.

14. An apparatus for testing a junction strength of an electrode as claimed in claim 13, wherein said material forming said covering portion is chromium or titanium.

15. An apparatus for testing a junction strength of an electrode as claimed in claim 11, wherein said predetermined amount of said solder is at least 0.015 mm$^3$.

* * * * *